(12) United States Patent
Peter et al.

(10) Patent No.: US 11,903,577 B2
(45) Date of Patent: Feb. 20, 2024

(54) KNOT TYING ACCESSORY

(71) Applicant: Ceterix Orthopaedics, Inc., Fremont, CA (US)

(72) Inventors: Stephen J. Peter, San Francisco, CA (US); Victoria C. Quitugua, Palo Alto, CA (US); Mark Y. Hirotsuka, San Jose, CA (US); Michael Murillo, Menlo Park, CA (US); Nifer B. Goldman, Redwood City, CA (US); Christopher P. Bender, Oakland, CA (US); Sarah-Marie Chan, San Francisco, CA (US)

(73) Assignee: Ceterix Orthopaedics, Fremont, CA (US)

( * ) Notice: Subject to any disclaimer, the term of this patent is extended or adjusted under 35 U.S.C. 154(b) by 1238 days.

(21) Appl. No.: 16/528,972

(22) Filed: Aug. 1, 2019

(65) Prior Publication Data

US 2019/0380705 A1     Dec. 19, 2019

Related U.S. Application Data

(63) Continuation of application No. 15/283,749, filed on Oct. 3, 2016, now Pat. No. 10,405,853.

(60) Provisional application No. 62/236,758, filed on Oct. 2, 2015.

(51) Int. Cl.
*A61B 17/04* (2006.01)

(52) U.S. Cl.
CPC ...... *A61B 17/0482* (2013.01); *A61B 17/0401* (2013.01); *A61B 17/0469* (2013.01); *A61B 17/0485* (2013.01); *A61B 17/0487* (2013.01); *A61B 2017/0417* (2013.01); *A61B 2017/0454* (2013.01); *A61B 2017/0462* (2013.01); *A61B 2017/0477* (2013.01); *A61B 2017/0488* (2013.01)

(58) Field of Classification Search
CPC ............ A61B 17/0485; A61B 17/0469; A61B 17/0482; A61B 17/0483; A61B 2017/0477; A61B 2017/0474; A61B 2017/0475
See application file for complete search history.

(56) References Cited

U.S. PATENT DOCUMENTS

| | | | | | |
|---|---|---|---|---|---|
| 5,454,821 | A | * | 10/1995 | Harm | A61B 17/0469 606/139 |
| 5,466,241 | A | * | 11/1995 | Leroy | A61B 17/12013 606/139 |
| 2003/0109891 | A1 | * | 6/2003 | Dana | A61B 17/0057 606/148 |

(Continued)

*Primary Examiner* — Diane D Yabut
(74) *Attorney, Agent, or Firm* — Norman F. Hainer, Jr.; Kate Ryland Tetzlaff

(57) ABSTRACT

Devices for easily and quickly tying complex suture knots are disclosed. The knot tying accessories described herein provide a means for introducing a complex knot pattern into a bight of suture using a device body and a guide thread. The device body includes system for maintaining the guide thread and suture in a convoluted pathway, either with the use of channels, protrusions, or a combination of both within its interior, on its exterior, or both. The guide thread may include a coupler at one end for holding a suture end while the guide thread leads the suture through the convoluted path defined within the guide body. Pull tabs may also be included to aid with exchanging the guide thread for the suture ends.

19 Claims, 20 Drawing Sheets

(56) References Cited

U.S. PATENT DOCUMENTS

2009/0234295 A1\* 9/2009 Lampropoulos ....... A61B 50/20
604/174
2010/0249809 A1\* 9/2010 Singhatat ........... A61B 17/0485
606/228

\* cited by examiner

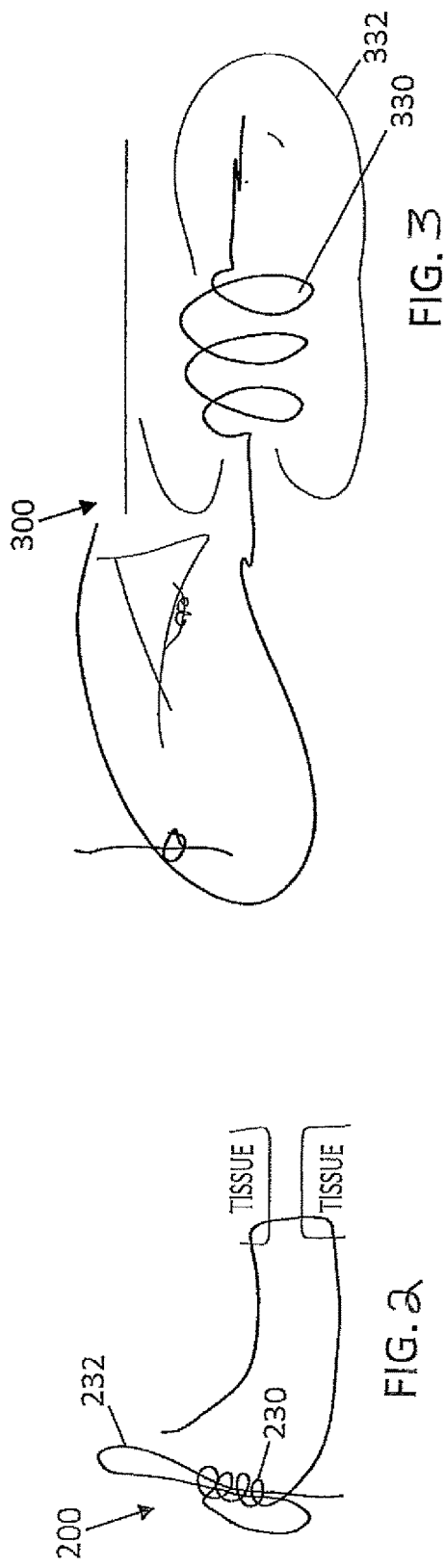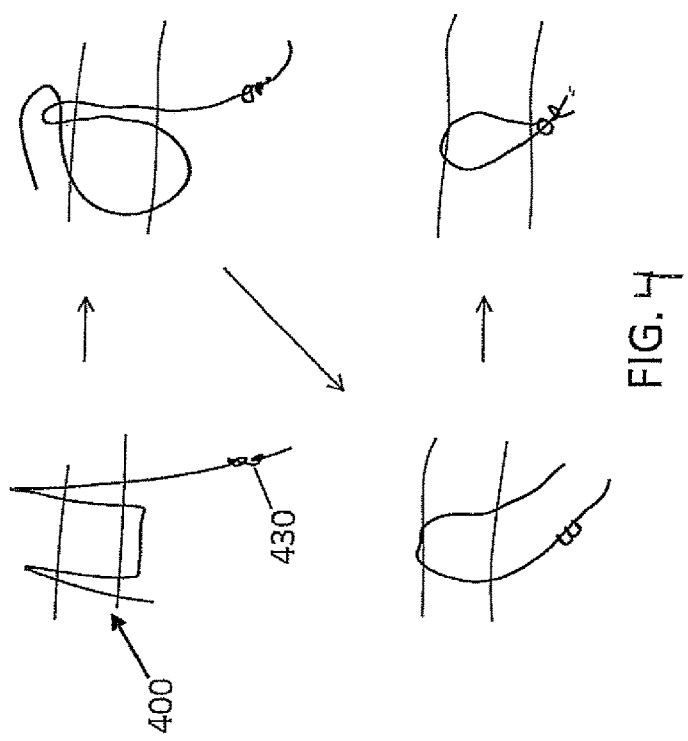
FIG. 3
FIG. 4
FIG. 2

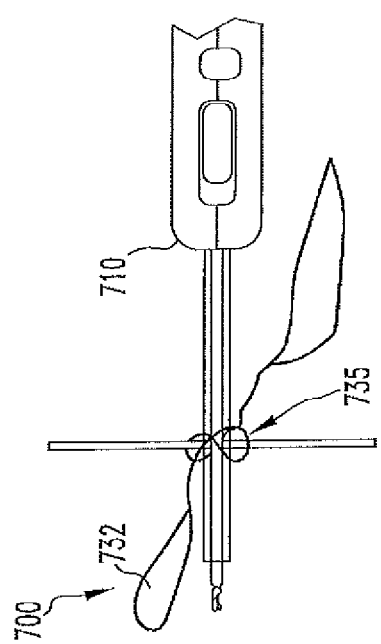
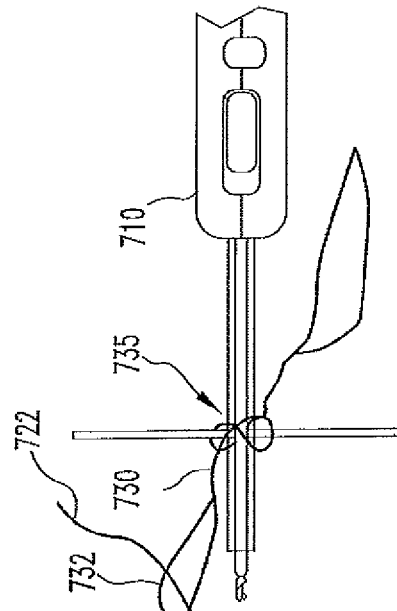
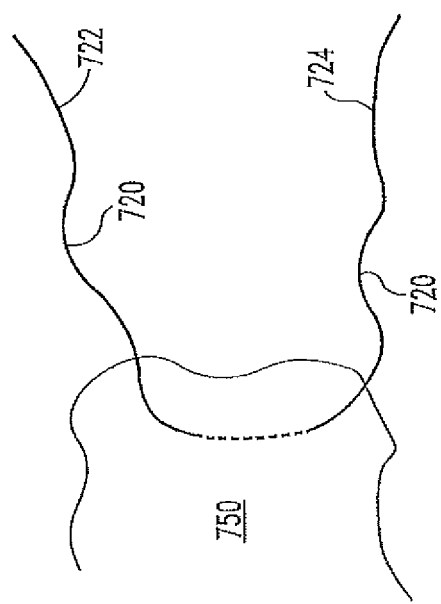
FIG. 7A
FIG. 7B

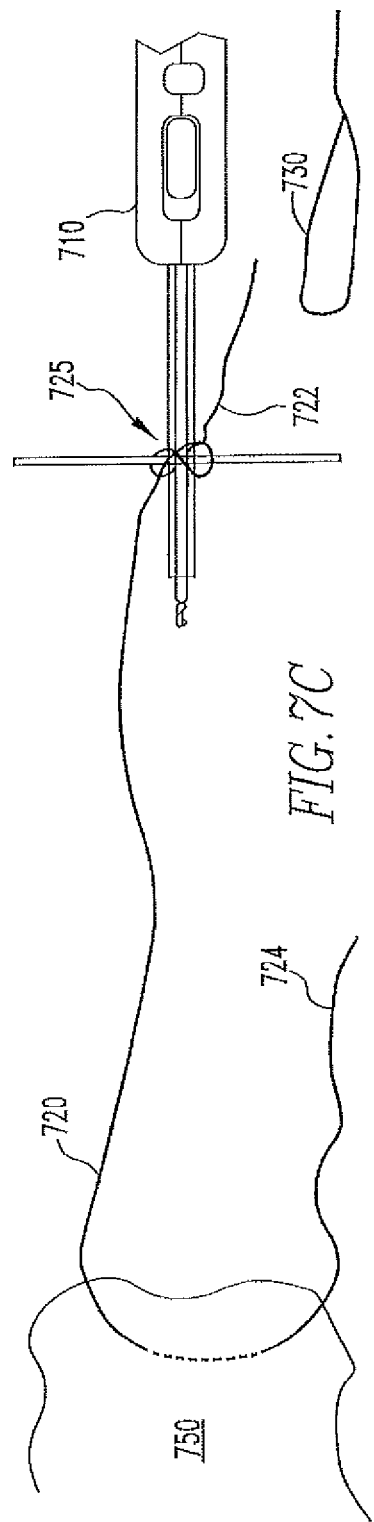
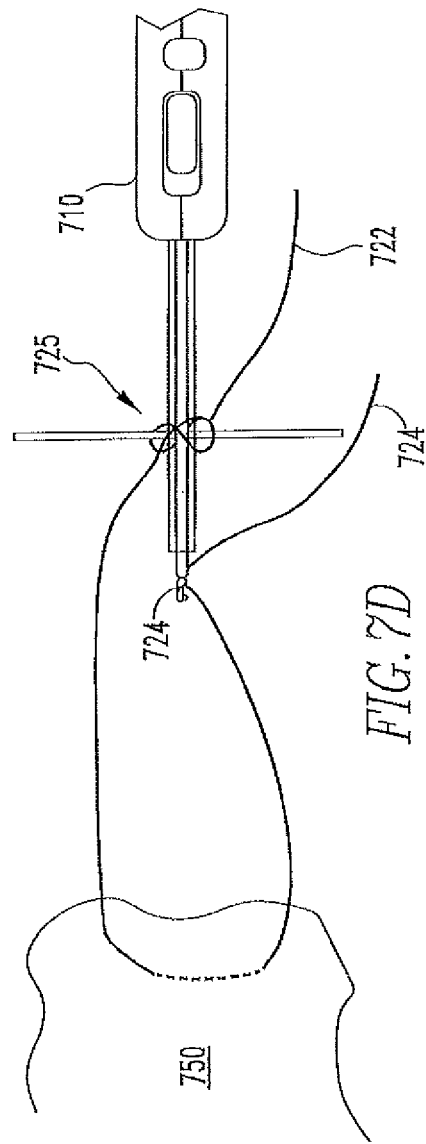

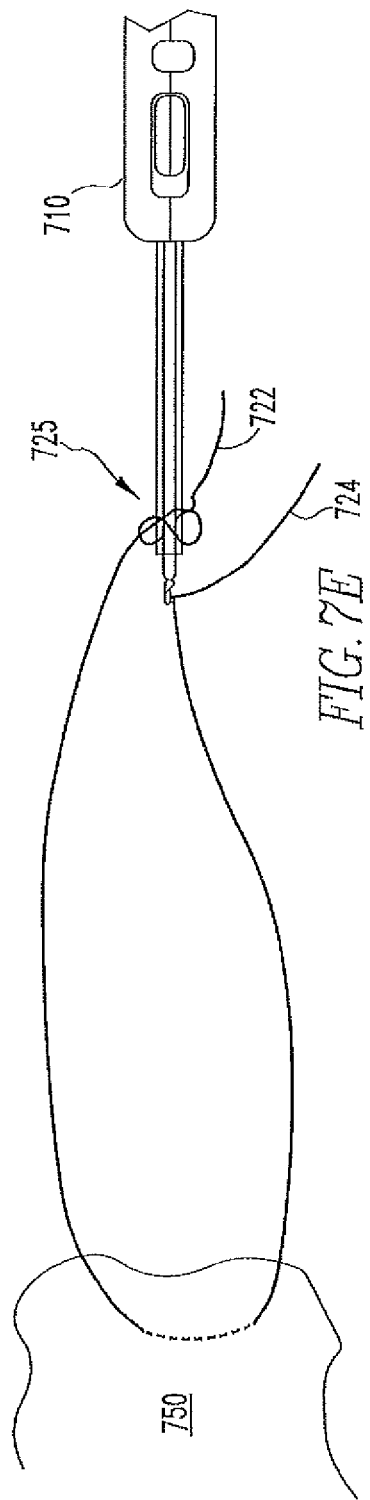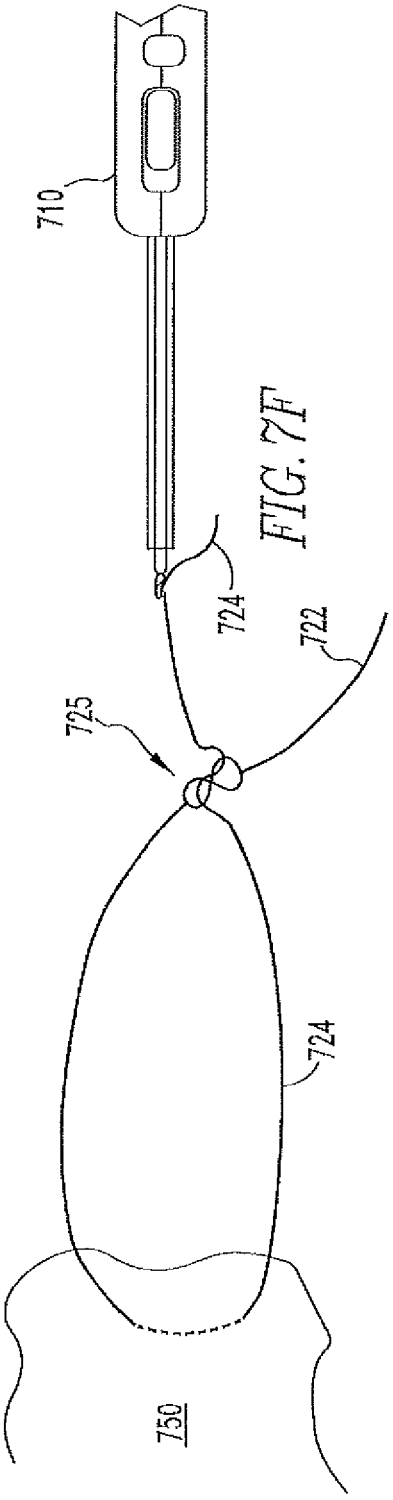

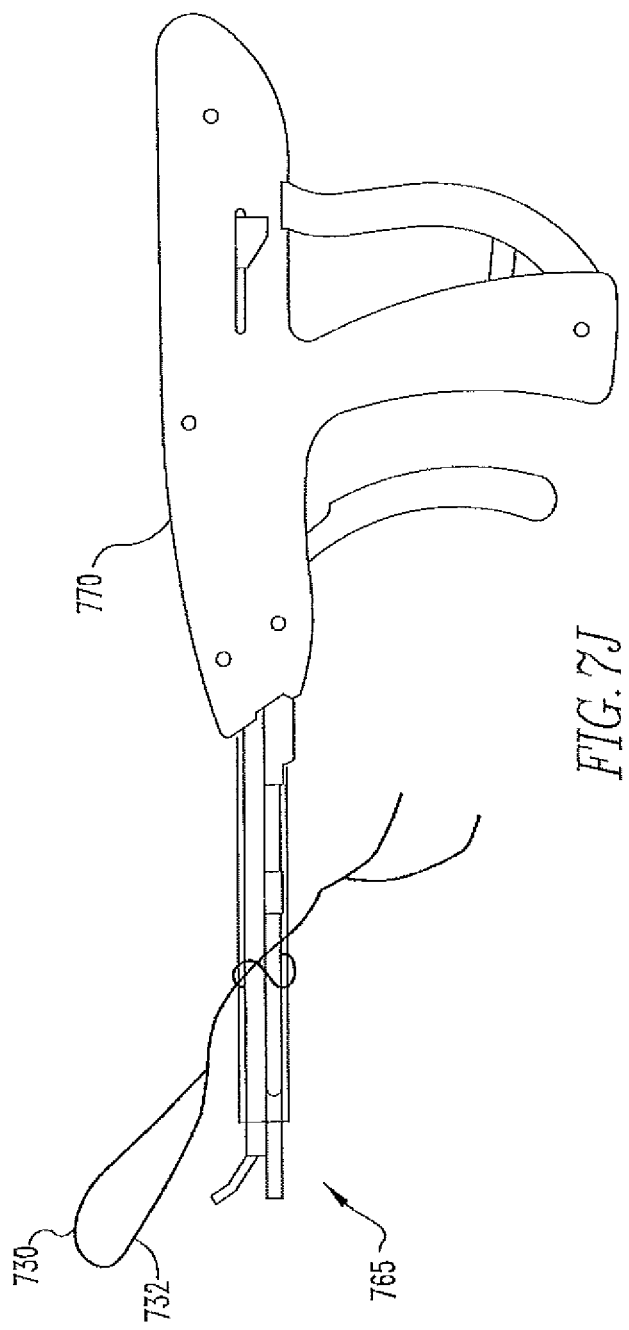

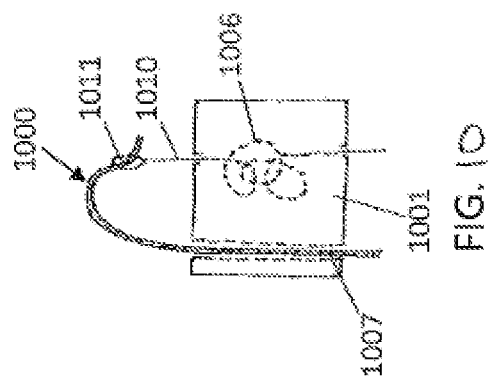
FIG. 10
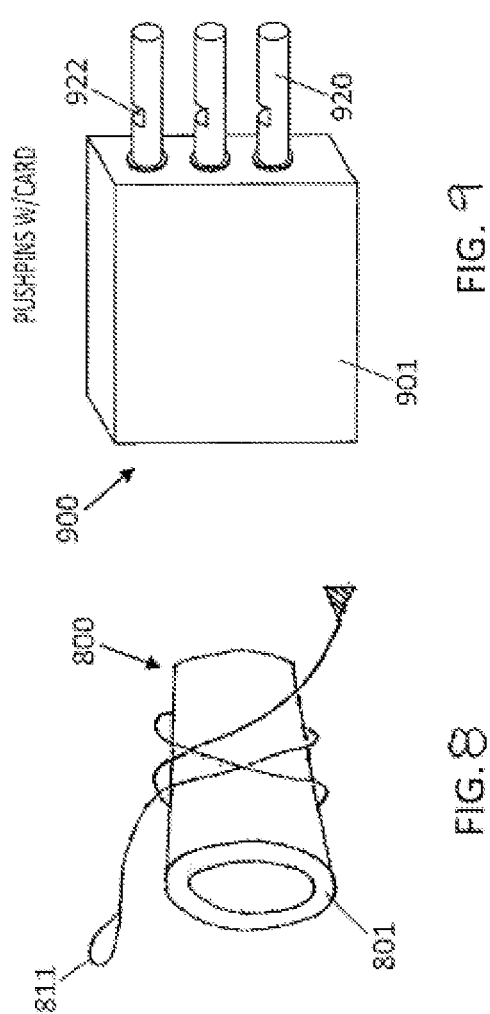
FIG. 9
FIG. 8

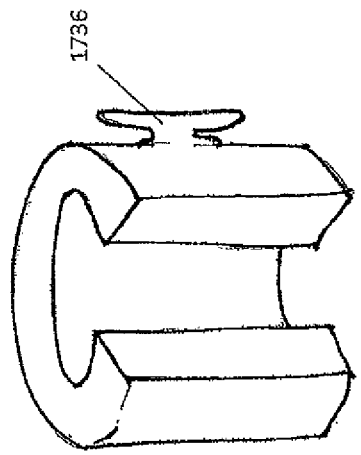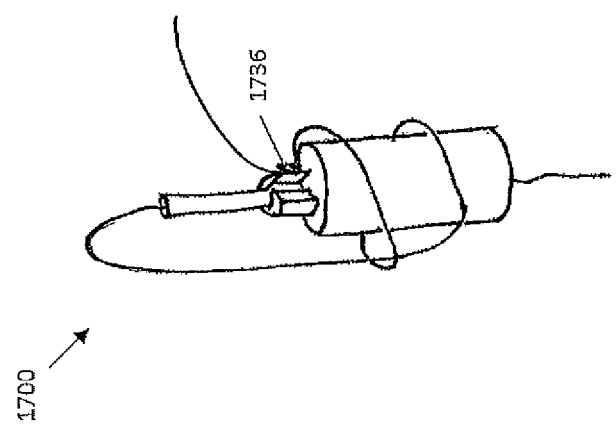

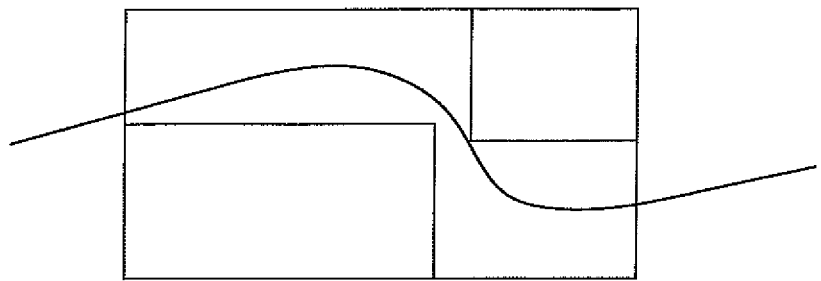
FIG. 22D
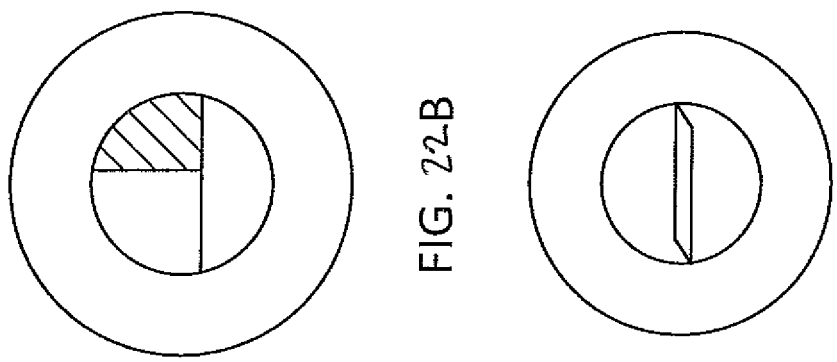
FIG. 22B
FIG. 22C
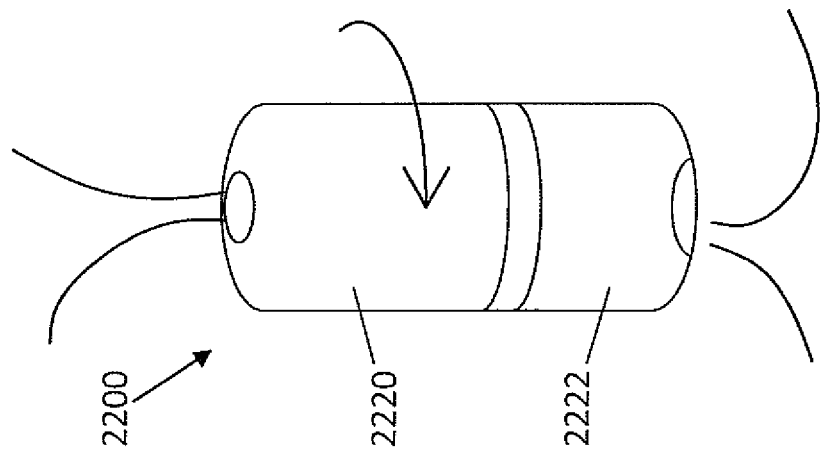
FIG. 22A

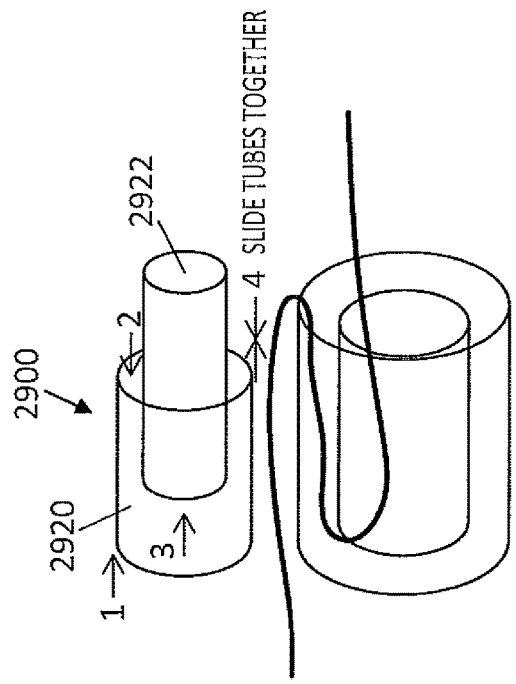
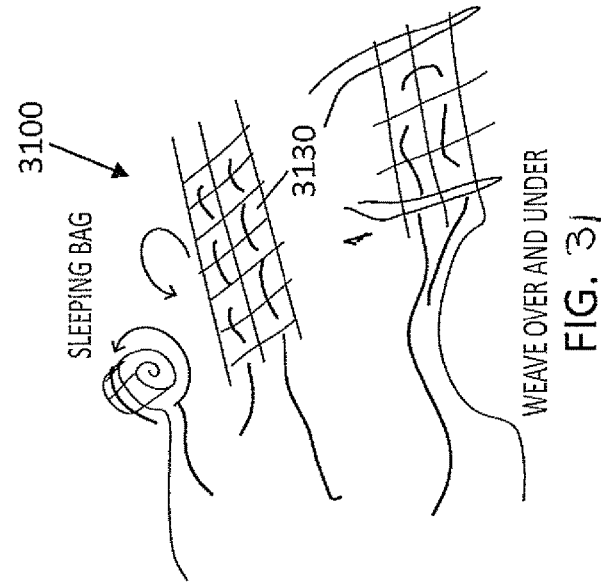
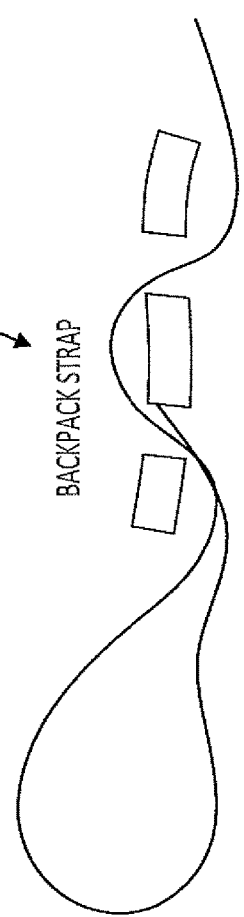
FIG. 28
FIG. 29
FIG. 30
FIG. 31

KNOT TYING ACCESSORY

CROSS REFERENCE TO RELATED APPLICATIONS

This application is a continuation of U.S. application Ser. No. 15/283,749 filed Oct. 3, 2016, which claims priority to U.S. Provisional Patent Application No. 62/236,758, filed Oct. 2, 2015 which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates broadly to medical devices and methods of their use. More particularly, the present invention relates to accessory devices, methods, and kits for tying knots in sutures.

BACKGROUND

Presently, sutures that are tied to maintain a wound in a closed position are hand-tied by the surgeon performing the procedure. Forming the suture knot and tying off the suture knot such that the knot does not slip or is too slack with respect to the tissue opening can be a challenging final step in what may already be a challenging and arduous procedure. In some instances, there is limited space and clearance for a surgeon to make the necessary movements of the tool or of their hand in the area that is being sutured, such as areas near bone. In those instances, tying a steadfast suture against the tissue to be held together may be challenging. Finally, while an operating room is technically sterile, it would still be advantageous to lessen the time an area being operated on is left open to potential infectious agents. Thus, decreasing the time it takes to tie off a suture is desirable.

While suture-related instruments such as suture passers and knot pushers have been developed to aid in reducing suturing time and suturing difficult to access areas of the body, these devices still fall short of being able to quickly tie adequate suture knots. For example, suture pushers may be able to stitch tissue even in hard to reach areas, but once a suture requires tying off, it is still a challenge for a surgeon to easily loop the suture ends together using a suture pusher.

Surgical staples are an alternative to sutures for quickly closing a wound. Unfortunately, surgical staples leave unpleasing closure marks upon healing. Thus, it would be desirable to have a device for providing an easy way to tie off a suture where there is no steep learning curve for using such a device.

SUMMARY OF THE DISCLOSURE

The present invention relates to devices, methods and kits for forming a simple or complex suture knot at a first and a second end of a piece of suture. The devices and methods disclosed herein are able to quickly and easily form a non-slipping knot that can be positioned close to the tissue sections to be closed. While it is contemplated that the knot tying accessories will be reusable, it is also contemplated that sterile kits be provide the have guide threads pre-threaded through the knot tying device ready for immediate use when needed.

The devices and methods described herein are for quickly tying off two free ends of a suture. The devices of the present invention comprise a guide body having internal pathways, a guide thread that is able to thread the guide body. The guide body can be opened and closed. In one example, the guide body includes openings disposed on the guide body where the sections of the guide thread is exposed at these openings. The guide body has a top and a bottom side that fit together when closed. The guide body may be opened to expose an interior space comprising a series of pathways that are disposed on the top and bottom side of the guide body. The series of pathways may be only on one side of the guide body or a complete pathway may be formed when the top and bottom sides are fitted together. In other instances, the pathways on the top and bottom are different and aid in forming different portions of the suture knot. The interior space including a convoluted pathway that crosses over itself at more than one location within the guide body. The convoluted pathway in some examples are essentially planar and a piece of guide thread can be wound in a particular pattern through the convoluted pathway.

The convoluted pathway with in the internal space of the guide body may include a series of channels in which the guide thread can be placed. In other examples, the convoluted pathway is delineated with posts or a series of protruding bodies that allow for the guide body to be wound past some or all of the posts or protruding bodies. There may be more than one path through the convoluted pathway that the guide thread can take when placed within the convoluted pathway. In some instances, the convoluted pathway may be defined by a combination of channels and protruding bodies. Whether the convoluted pathway is a series of channels, protruding bodies, or a combination of both, the path that the guide thread take within the guiding bodies generally take on soft curves able to easily slight within a channel or past the protruding bodies.

In an exemplary embodiment, the guide thread has a capture loop on one end while the other end is free. The length of the guide thread is such that there is not an excess of thread length once the guide thread has been laced through the desired channels or past the series of protruding bodies. Once properly placed within the guide body, the end of the guide thread having the capture loop extends from the guide body at a first location. A bight of guide thread is exposed at a second location with regard to the guide body, and the free end of the guide thread trails out of and away from the guide body at a third location.

The capture loop of the guide thread functions to securely hold a piece of suture so that the corresponding length of suture may be pulled through the entire length of the convoluted pathway without breaking free. The capture loop may also be a sliding knot that is able to cinch down and hold onto a piece of suture. In some examples, the capture is constructed from the same length of thread as the guide thread and is made from the same material. In other examples, the capture loop can be constructed from a material different than that of the guide thread. In some instances, the capture loop may be constructed from a metallic material. The capture loop may have a collapsible state for coupling and holding onto a suture end, and the capture loop may have an open state where the suture end is initially thread through the capture loop and when the suture is ready to be released after being threaded through the convoluted pathway of the guide body.

The knot tying device may also include pull tabs. The pull tabs are releasably coupled to the guide thread at locations where the guide thread is exposed with regards to the guide body. The pull tabs, when pulled in the proper sequence, aid a user in pulling the guide thread and the appropriate suture end through the convoluted pathway of the guide body such that the suture ends replace the guide thread within the convoluted pathway of the guide body.

The knot tying devices disclosed herein also have other forms that are able to maintain the guide thread in a particular pattern. In some other examples, the free suture ends may be directly threaded into the knot tying device, where the suture end may be wound around the device in a pattern for forming a knot. Some of the knot tying devices described below may be used in conjunction with existing suturing devices such a suture passer or a suture knot pusher.

In some examples of the knot tying device shown, no actual accessory device is provided for. In these embodiments, the suture itself has a unique element. For example, the suture may have a pre-formed knot bundle where the pre-formed knot bundle is maintained within a suturing device such as a suture passer or a suture pusher.

Also described herein are methods for using the various embodiments of the knot tying devices described. In some instances, instructions may be included with any of the knot tying devices included to aid the user in using the device. In other instances, there may be markings on the actual device for instructing the user on how to thread the guide thread within the convoluted pathway of the guide body and the order for pull the pull tabs that lead to replacing the guide thread with the suture ends.

Finally, also described herein are kits that may be provided for either a single use or multiple uses. The advantage of having a single use device is that the device will be maintained within a sterile environment until needed. Also, the surgeon performing the suturing will be ensured that he will have all the elements of the knot tying accessory at his disposal when the time comes for tying off a suture.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1B is a drawing showing the first embodiment where a first suture end threaded through the capture loop and where the first pull tab has started to be pulled. FIG. 1C is a drawing showing the first embodiment where the first pull tab has completely pulled the guide thread and now the suture end has replaced a portion of the thread guide within the guide body. FIG. 1D is a drawing showing the first embodiment where a second suture leg/end has been threaded through the capture loop after the capture loop has traveled through a portion of the guide body and exited at the second opening on the guide body. FIG. 1E is a drawing showing the first embodiment wherein the second suture leg/end has been pulled through a latter portion of the guide body. FIG. 1F is a drawing showing the first embodiment where the first and the second ends of the suture has been removed from the guide body and is ready to be tightened against portions of tissue being sutured.

FIG. 2 is a drawing of a second embodiment of a suture with a pre-formed knot bundle for securing tissue together.

FIG. 3 is a drawing of a third embodiment of a suture with a pre-formed knot bundle for securing tissue together.

FIG. 4 is a drawing of a fourth embodiment of a suture with a pre-formed knot bundle for securing tissue together.

FIGS. 7A-7J are photos showing a seventh embodiment having a cartridge containing a suture having a snare in a loose knot configuration that is attached around a knot pusher or a suture passer.

FIG. 8 is a drawing of an eighth embodiment of the knot tying accessory having a tubular-shaped device body 801 having a snare 811 wound around it in a knot bundle configuration.

FIG. 9 is a drawing of a ninth embodiment of the knot tying accessory in the shape of a card deck including a series of pushpins.

FIG. 10 is a drawing of a tenth embodiment of the knot tying accessory in the shape of a card deck and including snares and guides for creating a knot.

FIG. 11A shows the knot tying accessory in an open state while FIG. 11B shows the knot tying accessory in a closed state.

FIG. 16A shows a side view of this embodiment while FIG. 16B shows a top view.

FIGS. 17A and 17B are drawings of a variation of the sixteenth embodiment where the cam paths includes a cleat or cleats.

FIGS. 22A-22D is a drawing showing another embodiment of an implantable knot tying accessory device having a rotatable clasp. FIG. 22B shows a top view where the top and bottom portions of the clasp are aligned. FIG. 22C is a top view of the accessory where the top and bottom portions of the clasp are not aligned. FIG. 22D is a cross-sectional view of the device.

FIG. 28 is a drawing of another embodiment of the knot accessory showing an implant similar to a backpack strap.

FIG. 29 is a drawing of another embodiment of the knot accessory with a tubular construction having an inner 28 is a drawing of another embodiment of the knot accessory showing an inner and an outer tube.

FIG. 30 a drawing of another embodiment of the knot accessory showing a suture bight through a hole in an implant.

FIG. 31 is a drawing of another embodiment of the knot accessory showing a mesh/grid material through which the suture is woven for maintaining the suture.

DETAILED DESCRIPTION

Figures 1A, 1B, 1C:
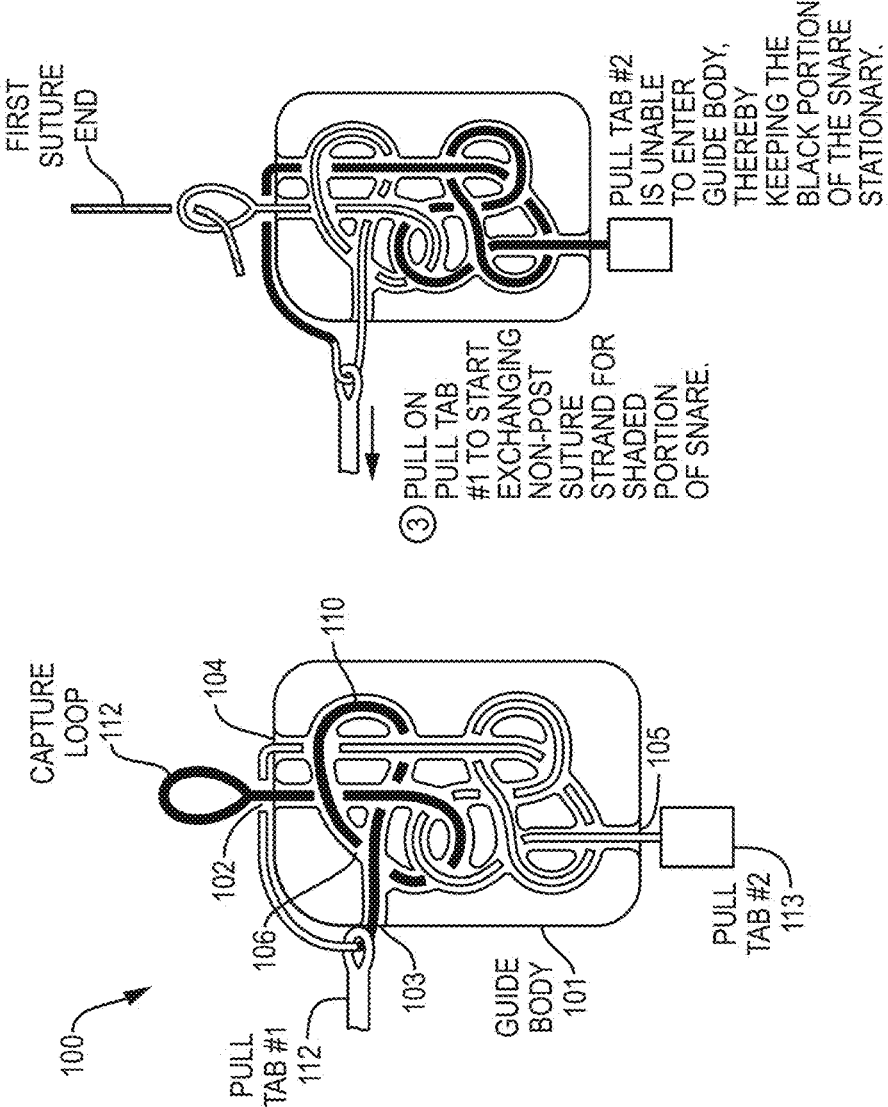
FIGS. 1A-1F are drawings of a first embodiment of a knot tying accessory where a guide thread with has been placed within a convoluted path of a guide body. The guide thread includes a capture loop at one end. A first and a second pull tab are shown attached to the guide thread.

Described herein are devices for aiding a healthcare professional with tying secure suture knots quickly and easily. In general, the knot tying accessory includes a guide body and a plurality of guides within or on the surface of the guide body for winding a piece of guide thread or suture through. In some embodiments of the knot tying accessory device, the device includes capture loops disposed on the end or ends of the guide thread that aid in pulling the suture ends through the guide body to form a particular knot pattern.

In general, the guide body is a first portion of the knot tying accessory device. The term "guide body" is used to describe portion of the device that is able to accept and retain the piece of guide thread or the piece of guide thread coupled to a bight of suture. The guide body can be any particular shape. In some of the examples, the guide body is in the shape of a rectangular case. The guide body in some instances can be opened to expose an interior space that is defined by channels. The guide body may also include a series of openings where the guide thread is first threated and where portions of the guide thread is accessible.

The guide body may be constructed to resemble a puzzle having openings or couplers. In these instances, the guide thread or the bight of suture may be coupled in a particular way about the guide body. After the guide thread or the suture has been coupled to the guide body, portions of the guide body is able to rotate in a particular sequence to form a knot. In the case, where the guide thread is used, the guide thread would then couple to the end of a suture and be used to pull the suture through the path about the guide body. Once the knot has been formed, the guide body is able to release the knotted suture, where the knotted suture may then be cinched down against the tissue.

The guide body may be constructed of any suitable materials such as plastics, metals, and other natural, man-made materials, or some combination thereof. In some instances, there may be instructions or directions on the guide body to aid the user in lacing the guide thread or the suture in the device body. The instructions may be arrows, numbers, wording, or pictures that show how to thread the guide thread or suture through the device.

In general, the term "convoluted pathway" as used in this disclosure means the path or paths defined within the interior space, the outer surface, or a combination of inner and outer surface that is able to define a pathway, where the pathway may cross over itself at multiple points throughout the path. In some embodiments, the guide body includes channels within its interior space that define the convoluted pathway. In other embodiments, instead of channels, posts or other protrusions may be included within the interior space of the guide body for lacing the guide or suture thread through the convoluted path. Also, a combination of channels and/or protrusion may also be used. In some examples of the channels and/or protrusions that define the pathways available for the guide or suture thread are stationary and thus able to only define a limited number of convoluted pathways within the guide body. In other examples, the channels and/or protrusions that define the convoluted pathway may be adjusted to form new pathways through which the guide or suture thread may be laced to form new knot patterns.

Typically the convoluted pathways that the suture and guide thread will take has a sweet spot with regards to the angles of each of the turns that the path would take. It would not be desirable to have the guide or suture thread move past a sharp ninety degree angle as this would cause much friction and may case the guide or suture thread to be caught within the device body. It is thus preferable to have the pathway that the guide or suture thread travel be curved or straight to reduce the amount of friction when the guide or suture thread experiences while being pulled through the convoluted pathway.

In general, the term "guide thread" is used to describe a line that is able to couple with a bight of suture. The guide thread is pre-laced within the guide body prior to coupling with the bight of suture. The guide thread may be constructed from a thread made of natural or synthetic material. One criterion is that the guide thread be easily pulled within the convoluted pathway of the guide body. In some instances, the guide thread may be coated with a material having a low coefficient of friction. In other instances, a lubricating substance may be interwoven into the thread fibers. The coefficient of friction being less than 0.5 or less than 0.1.

In some of the embodiments of the knot tying accessory device, the guide thread includes a "capture loop" at one end. In general, the capture loop functions to couple with the bight of suture and to pull the suture through the convoluted pathway for forming a knot. The capture look may be of the same material as that of the rest of the guide thread or of a different material. In some examples, the capture loop is a piece of thread-like material and may be cinch down onto the bight of suture like a sliding knot. In other examples, the capture loop may contain a mechanism for clamping down and grabbing the bight of suture for drawing the bight of suture through the guide body and then releasing the bight of suture once the suture has been drawn through the desired portions.

The knot tying accessory may also include "pull tabs". In general, "pull tabs" are tabs or pulls that can couple to portions of the guide thread that are exposed when the guide thread has been threaded within the guide body. The pull tabs can be of any suitable shape or size as long as they are easy to pull and grip. The pull tabs may be able to couple to the bight of suture through a coupler such as a clip.

A first embodiment of the knot tying device 100 is shown in FIGS. 1A-1F. Device 100 includes a device body 101; a series of openings, 102, 103, 104, and 105; an interior pathway 106; a guide thread 110, and a first and a second pull tab 112 and 113, respectively. In this embodiment, the device is largely rectangular but the device body can take on any shape suitable for having an internal pathway that can guide a line such as a thread to be tied into a knot pattern. In some examples, the device is openable to show the interior pathway. A user can then thread the guide thread 110 through the interior pathway 106 to arrive at what is shown in FIG. 1A. In some instances, there may be instructions on the device body using arrows, numbers, or other suitable instructions to aid the user in threading the guide thread through the interior pathway. In other instances, there may be separate instructions on how to thread the guide thread through the interior pathway. There may also be multiple ways that a line may be threaded through the interior pathway for forming a knot.

FIG. 1A shows the guide thread 110 already laced through the interior pathway 106. The interior pathway 106 will typically have a convoluted route for forming a complex knot wherein the path forces the line following its path to cross over on itself at least once and often times more than once. FIG. 1A also shows that the guide thread 110 also includes a capture loop 111 that is disposed on an end of guide thread 110. The guide thread 110 is a contiguous piece of material. The capture loop 111 in FIG. 1A is shown at opening 102. The guide thread comprises a single piece of material. The lighter color portion of the guide thread 110 shown in FIGS. 1A-1F are for showing the portion of the guide thread 110 that will be exchanged with a first end of a suture.

FIG. 1B shows the next step where the first end of a piece of suture is inserted through capture loop 111. A user can then pull the first pull tab 112 to start the exchange of the guide thread 110 with a portion of the first end of the suture where the first end of the suture enters the interior pathway 106 of the device body 101 at opening 102. Note here that the first pull tab 112, located at opening 103, can only easily pull on one side of the guide thread 110. In the setup shown for this embodiment, the second pull tab 113 prevents the upper or left portion of the guide thread 110 from being pulled through the interior pathway 106 and only the right or lower portion of the guide thread 110 is able to be pulled through the interior pathway 106.

FIG. 1C shows the resulting configuration once the first end of the suture has completely replaced the first portion of the guide thread 110 within the interior pathway 106. Here, the capture loop 111 end of the guide thread 110 has exited the first portion of the interior pathway 106. The first pull tab 112 can be uncoupled from the guide thread 110. Next, the user can pull second pull tab 113 which is attached to a second, free end of the guide thread 110. This brings the capture loop 111 to the opening 104.

Figure 1F:
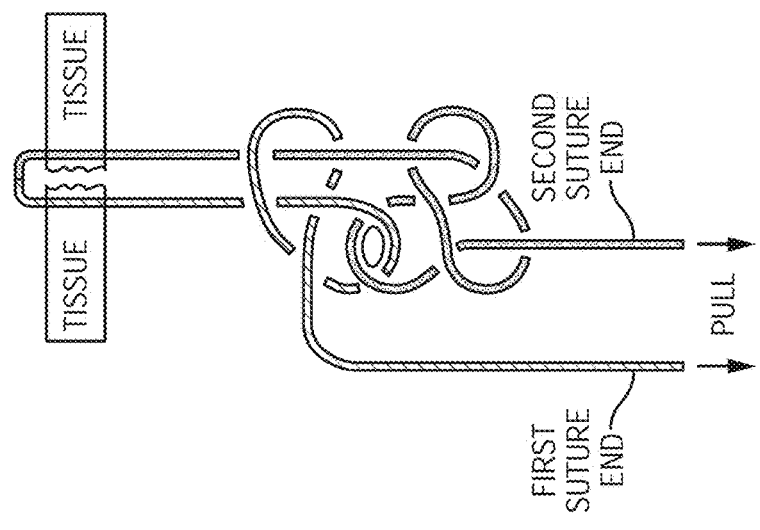
Figure 1E:
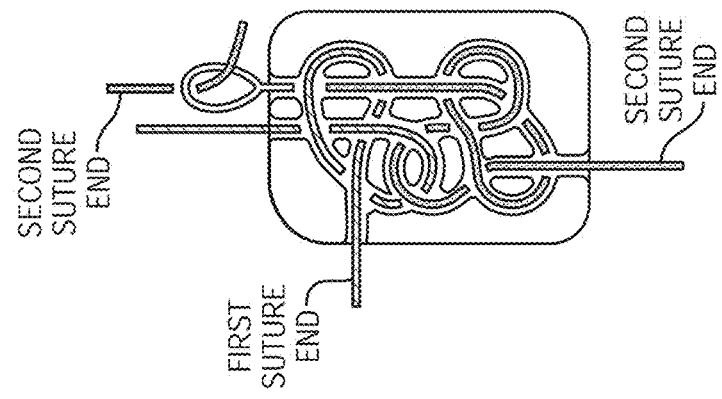
Figure 1D:
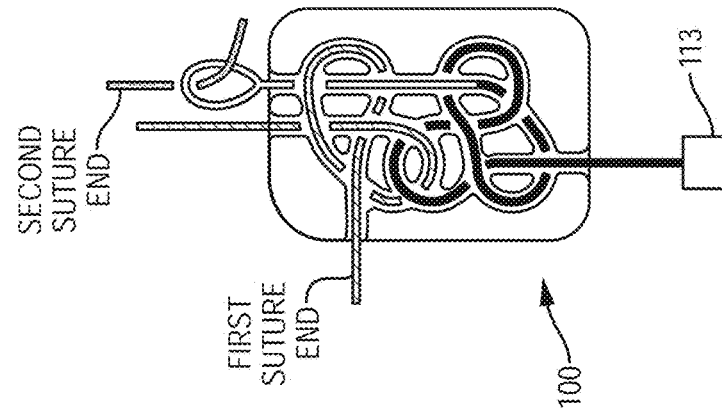

Turning to FIGS. 1D, 1E, and 1F, the capture loop 111 is shown being coupled to a second end of the suture in FIG. 1D. The user can pull on the second pull tab 113 which starts the replacement of the latter portion of the guide thread 110 with the second end of the suture. The user will continue to pull on the second pull tab 113 until the second end of the suture starts to exit from opening 105. At that point, the entire interior pathway 106 has been replace with the first and the second suture ends. Finally, FIG. 1F shows the loose knot configuration after the user has removed the device from the knot. The knot bundle than can be cinched against the tissue to hold the suture together.

Turning to FIG. 2, a suture having a pre-formed knot bundle 230 at a first end is shown. The preformed knot bundle 230 may also include a loop 232 at a first end of the suture. The pre-formed knot bundle 230 may be pre-loaded into a suturing device, such as a suture passer, where the pre-formed knot bundle 230 may be entirely contained within the suture or reside on the outside of the suture passer. The knot bundle 230 may be passed through tissue at a first location and a free end of the suture is passed through tissue at a second location. The free end of the suture is then able to pass through the loop 232, where the knot formed may be tightened into a final position against the tissue to complete the repair.

Turning to FIG. 3, a third embodiment of a knot tying device 300 is shown. In this embodiment, a pre-tied knot bundle 330 is located at a first end of the suture. The pre-tied suture may be pre-loaded into a suture device such as a suture passer. Unlike the previous embodiment, the pre-tied knot bundle 330 is not passed through the tissue. A long loop 332 that extends from the knot bundle 330 may be passed through the tissue at a first location, and a second send of the suture is passed through the tissue at a second location. The second end of the suture may then be passed through the loop 332 and the loop 332 is then used to pull the second end of the suture through the tissue and into the knot bundle 330. The knot coupling the knot bundle 330 and the second end of the suture is then tightened into a final position to complete the repair. In other examples, the pre-tied knot bundle may include loose loops of suture that can facilitate the insertion of the second end of the suture (the free end of the suture) into the pre-tied knot bundle.

FIG. 4 shows a fourth embodiment of a knot tying device 400 having a suture with a pre-tied knot bundle 430 at a first end of the suture. The pre-tied knot bundle 430 may also be pre-loaded into a suture device such as a suture passer. Similar to the previous embodiment, the pre-tied knot bundle 430 is not passed through the tissue. A bight of suture adjacent to the pre-tied knot bundle 430 is passed through tissue at a first location and the free, second end of the suture is passed through tissue at a second location. The pre-tied knot bundle 430 is then passed through the bight of suture and the bight of suture is then used to pull the free, second end of the suture through the tissue. The free, second end of the suture is then passed through the pre-tied knot bundle to form a completed knot, and the completed knot can then be tightened into its final position to complete the repair.

Figure 5:
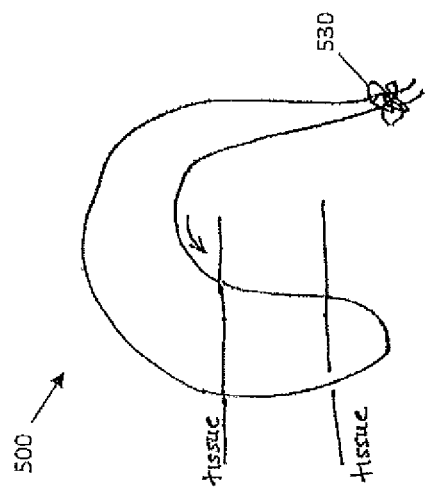
FIG. 5 is a drawing of a fifth embodiment of a suture with a pre-formed knot bundle for securing tissue together.

FIG. 5 shows a fifth embodiment of a knot tying device 500 having a pre-tied knot bundle 530 disposed on a first end of a suture. In this embodiment, the pre-tied knot bundle 530 is intended to be part of a suture subassembly. This suture assembly may be shuttled into the tissue where this is accomplished by using a first suture that has already been passed through tissue to shuttle the suture subassembly through tissue, exchanging the first suture for the suture subassembly. A free, second end of the suture subassembly may then be passed through the pre-tied knot bundle, and the suture subassembly can be shuttled through the tissue and through the pre-tied knot bundle in a single operation. The completed knot is then tightened into its final position to complete the repair.

Figure 6:
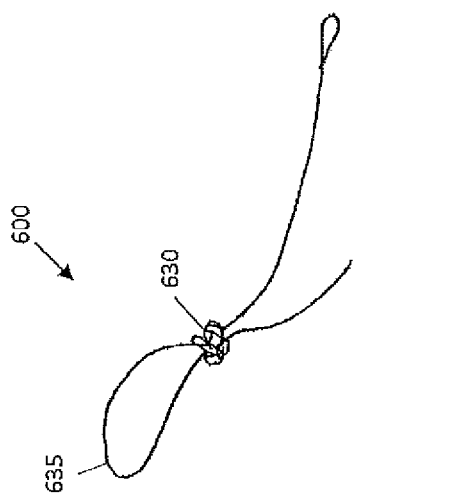
FIG. 6 is a drawing of a sixth embodiment having a sliding knot that is formed with a snare incorporated into a pre-formed knot bundle.

In yet another variation of some of the previous embodiments, a suture includes a pre-tied knot bundle disposed at a first end of the suture that can be part of a suture subassembly. In this embodiment, the suture subassembly may be contained within a knot pusher. The suture contained in the knot pusher is configured such that when a free, second end of the suture is shuffled through the tissue and back through the pre-tied knot bundle, the suture is already conveniently loaded with the completed knot at the end of the knot pusher. This embodiment would not require the additional steps of leading the suture by hand into the knot pusher FIG. 6 shows a sixth embodiment of a knot tying accessory 600. This embodiment includes a sliding knot 634 that is formed with a snare 635 incorporated into a pre-formed knot bundle 630. In some examples, the complete knot may be provided in a pre-tied configuration or it may be formed through an accessory device. The complete knot would first slide down a post-tissue leg of the suture. The post-tissue leg may then be inserted into a snare and pull through the knot, forming a convoluted pathway of the post-tissue leg through the knot. This configuration provides a more secure knot that would not slide as easily as the original knot.

FIGS. 7A-7I shows a seventh embodiment including a cartridge containing a suture having a snare 730 in a loose knot configuration 735 that is attached around a knot pusher 710. Once the suture 720 has been passed through tissue 750, a first end of the suture 722 is loaded into an open end 732 of the snare 730 in the cartridge, best seen in FIG. 7B. The snare 730 may then be pulled to form the suture 720 into a loose sliding knot configuration 725, shown in FIG. 7C. A second end 724 of the suture 720 is then loaded into the knot pusher 710 to form a post-tissue leg of the suture. The loose knot configuration bundle 725 is then released from the cartridge and transferred over the post-tissue leg 724 of the suture, shown in FIG. 7F, where it is then slid down into a final position and tightened to complete the repair knot 725', schematically shown in FIG. 7G.

Figure 7G:
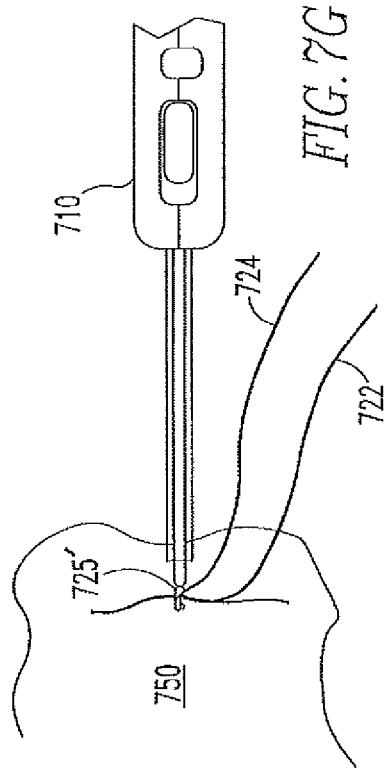
Figure 7H:
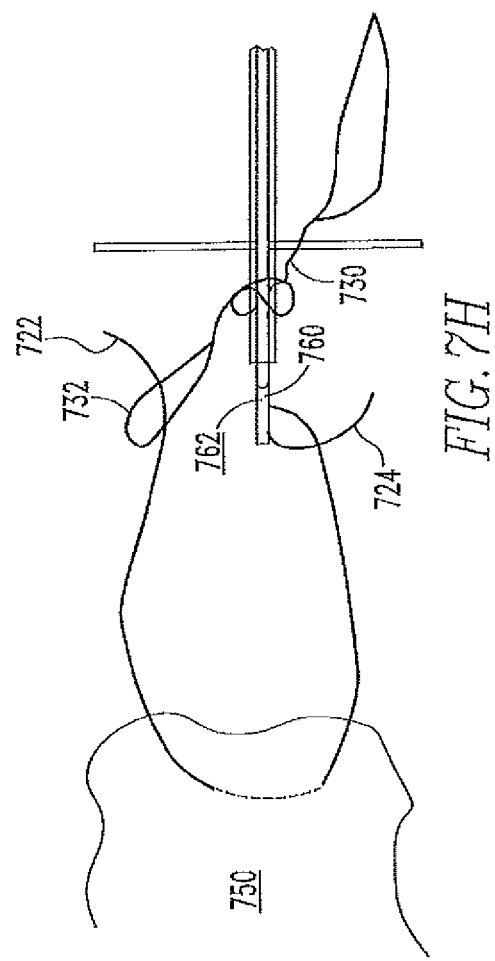

In a variation of the previous embodiment, the knot tying accessory includes a cartridge containing a snare 730 in a loose knot configuration that is wound around a suture passer 760 (FIG. 7H). Once the ends of a suture (722 and 724) have passed through tissue and are captured within the jaws 762 of the suture passer, a first end of the suture 722 is removed from the suture passer jaw and is then loaded into the open end 732 of the snare in the cartridge, best seen in FIG. 7G. The snare 730 is then pulled to form the first suture end into a loose sliding knot configuration (not shown, but similar to FIG. 7E). The loose knot configuration is then released from the cartridge and transferred over the second end 724 of the suture that remains attached to the suture passer jaw, similar to FIG. 7F. The complete knot is then slid down into its final position and tightened to complete the repair loop.

Figure 7I:
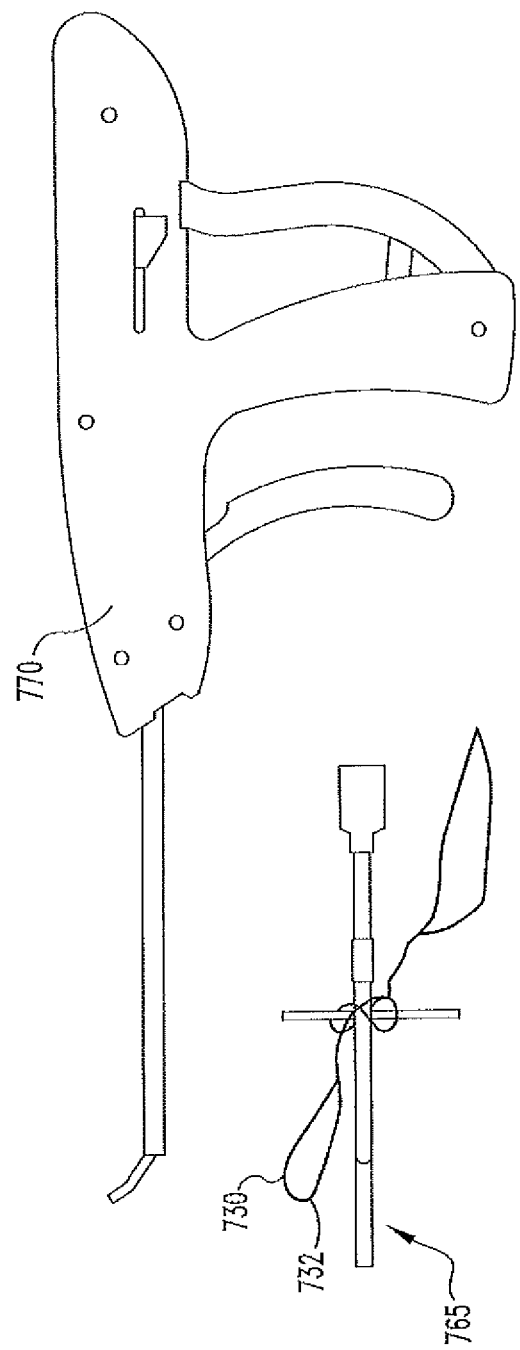

In yet another variation of a previous embodiment, the knot tying accessory includes a cartridge 765 that is designed with components to pass a preloaded suture (best seen in FIGS. 7I and 7J). Also included are components to facilitate forming a knot into a loose sliding knot configuration, such as a snare 730. The cartridge may be loaded into a suture passer handle 770. Both ends of the preloaded suture may be delivered through tissue and captured by a suture passer jaw. A first end of the suture can be removed from the suture passer jaw and loaded into a receiving component in the cartridge, such as an open snare 732. The first end of the suture is the pulled via the components into a loose sliding knot configuration. The loose knot configuration is then released from the cartridge and transferred over the second end of the suture remaining attached to the suture passer jaw. By pulling back on the suture passer handle, the remaining second end of the suture is deployed from the cartridge and the complete knot is slid down into its final position to complete the repair loop.

An eight embodiment of the knot tying device 800 (FIG. 8) includes a tubular-shaped device body 801 having a snare 811 wound around it in a knot bundle configuration. After the suture is laced into place, a first suture end is loaded into the receiving/open part of the snare 811, and when the snare 811 is pulled, the first suture end is pulled into the loose sliding knot configuration. The second end of the suture is threaded through the device body 801 and becomes a stem for the knot. Pulling the stem pulls the loose knot bundle off the device body and creates a sliding knot on the stem. In some examples, the device body is tapered, which aids in having uniform tightening of the knot bundle. In other examples, the device body may be collapsible allowing the knot to be easily pulled off. In yet another example, the device body includes pins or other forms of protrusions that are able to separate different portions of the snare winding elements. This layout allows for the formation of a knot through discrete phases (i.e. for a Revo knot, an underhand hitch, followed by another underhand hitch, followed by an overhand hitch).

A ninth embodiment of the knot tying device 900 (FIG. 9) includes a device body 901 that is in the shape of a card deck. The device body 901 includes a series of pushpins 920 each having notches 922 for forming a completed knot. A bight of suture is placed in the appropriate notches 922 of each pushpin 920 and with the aid of internal components, by pushing the pushpins 920 in a particular sequence forms a knot with the desired configuration.

A tenth embodiment of the knot tying device 1000 is shown in FIG. 10. Here, the device body 1001 is in the shape of a card deck. Device 1000 includes snare 1011 wound around guides 1106. The guides may be channels (as shown) or post/protrusions within the device body for guiding a guide thread 1010. A first suture end is snared through the device body 1001. In the example where only one snare is present, the second suture end is inserted through a channel 1107 in the device body 1001. The completed knot can then be released by opening or breaking apart the card-shaped device body 1001. In some examples, portions of the device body can be constructed from a foam material such that the knot can be pulled to release from the card-shaped device body. In other examples, the card-shaped device body may include two halves coupled wherein the completed knot may be released by unfolding the card. The two halves of the device body may have a hinged arrangement or may be slidingly coupled.

Figure 11B:
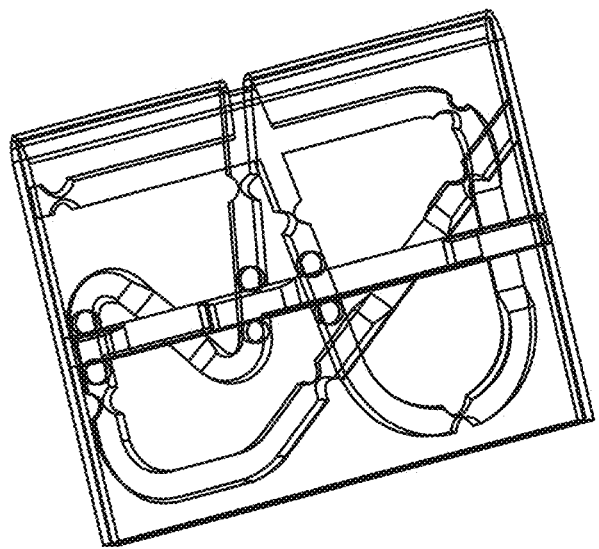
FIGS. 11A and 11B are drawings of an eleventh embodiment of the knot tying accessory having internal pathways disposed on an upper and a lower portion of a device body for forming a knot pattern.
Figure 11A:
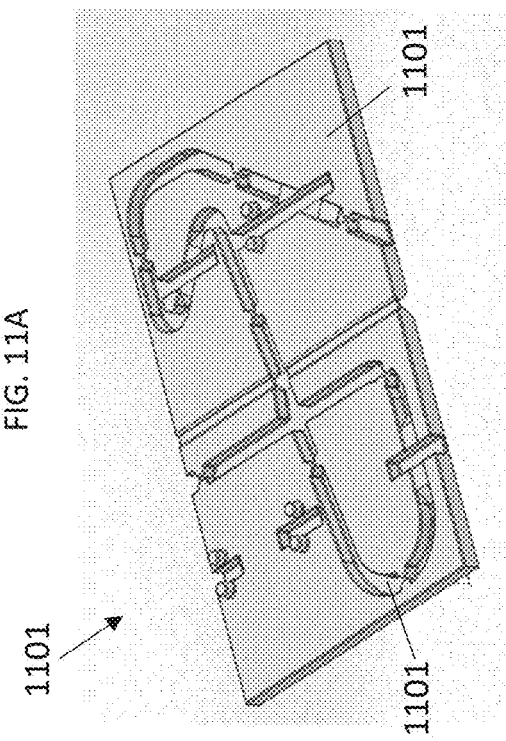

Turning to FIGS. 11A and 11B, an eleventh embodiment of the knot tying device 1100 is shown. In this embodiment, the device body 1101 also has a rectangular form. No capture loop is used. The user opens the device body (the open device body is shown in FIG. 11A). The user then lays a first end of the suture into the appropriate interior pathways 1106. The internal pathways may be channels or may be posts or other suitable element for retaining a bight of thread. Note that the device body is divided into an upper portion and a lower portion where the pathways of the upper portion is not necessarily the same as that for the lower portion. As before, there may be instructions imprinted on the actual device or there may be separate instructions for how to place a guide thread within the interior pathway 1106 of device 1100. The user then closes the device and inserts a second end of the suture the internal pathway 1106 (channels in the case), where the channels have the appropriate lead-ins to aid the second end of the suture cross under and/or over the first end of the suture. Once the second end of the suture has exited the device 1100, the device 1100 may be opened to release the formed knot.

Figure 12:
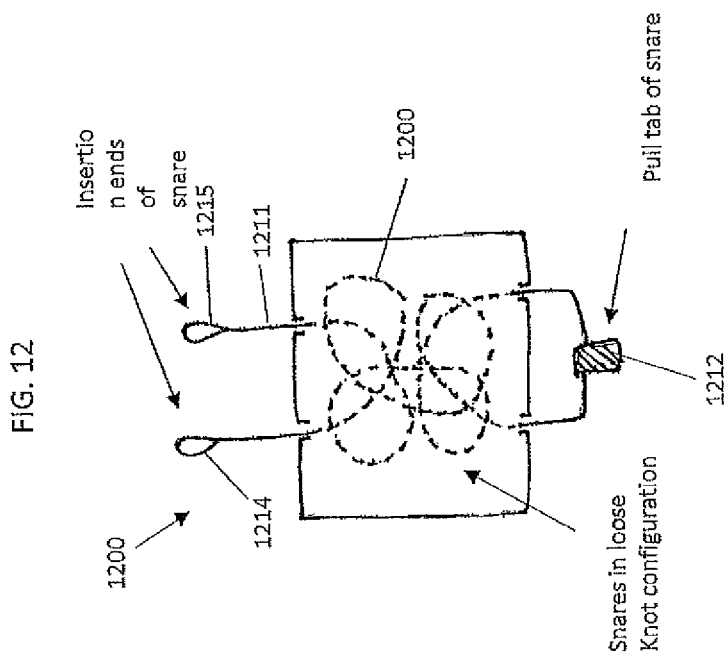
FIG. 12 is a drawing show a twelfth embodiment of the knot tying accessory having a snare, a first and a second insertion end, and a pull tab.

A twelfth embodiment of the knot tying device 1200 is shown in FIG. 12. Device 1200 includes one single length snare 1211 having a first and a second insertion end 1214 and 1215 and a pull tab 1212. The two legs of snare 1211 may form a loose knot configuration from being threaded through an interior pathway 1206. Snares 1214 and 1215 are able to couple with a first and a second end of a suture and the loose knot configuration may be transferred to the suture when the first and the second of the suture are pulled through a device body 1201 using the pull tab 1212.

Figure 13:
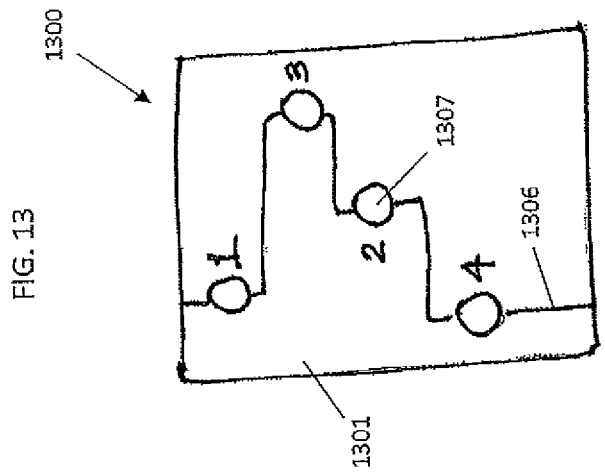
FIG. 13 is a drawing show a thirteenth embodiment of the knot tying accessory having a series of apertures 1307 that are connected with interior pathways.

A thirteenth embodiment of the knot tying device 1300 is shown in FIG. 13. Device 1300 also include a device body 1301 in the shape of a card deck. Device 1300 also includes a series of apertures 1307 that are connected with interior pathways 1306. Simple instructions may be provided to a user for inserting the suture through the apertures 1307 in a sequence that result in a desired knot formation. The device body 1301 may then be open or broken apart to release a completed knot.

In a variation on the previous embodiments of the knot tying device having an interior pathway, this embodiment includes a straight channel for insertion of a post-tissue suture end and instructions for a sequence of winding to form a sliding knot (e.g. a taut line hitch formed by wrapping twice around a distal portion of a tool and once around a proximal end of the tool). The card-shaped device body also includes cleats for holding the two regions of the knot separate to aid in winding the desired pattern.

Figure 14:
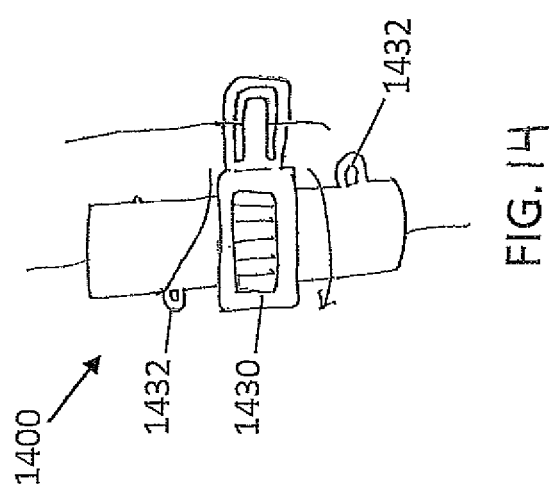
FIG. 14 is a drawing show a fourteenth embodiment of the knot tying accessory having a rotating piece and positioning aides for a winding tool to wind a suture into a correct knot pattern.

In yet another variation of the knot tying accessory device 1400, the device body may include a rotating piece 1430 and positioning aides 1432 for a winding tool to wind a suture into a correct knot configuration (FIG. 14). In some examples, a first end of a suture is secured to a carriage. The carriage is rotated and translated on the tube to tie the suture tail. The post-tissue second of the suture is inserted in the tube and the knot is slid off the tube onto the post.

Figure 15:
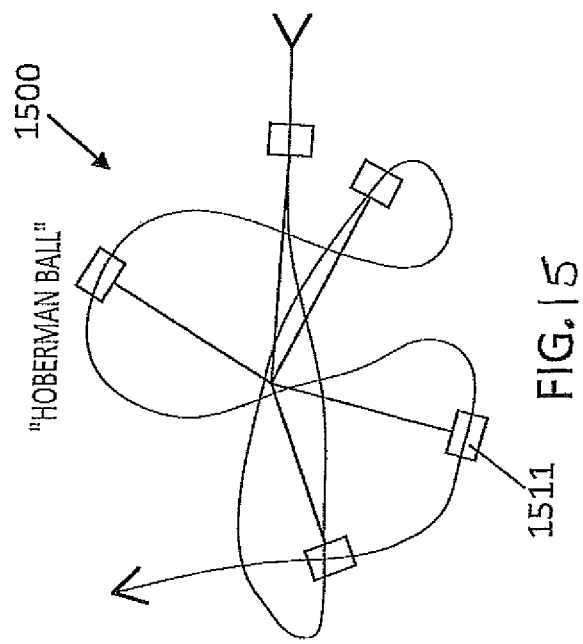
FIG. 15 is a drawing show a fifteenth embodiment of the knot tying accessory having a 3D geometric shape.

In yet another variation of the knot tying accessory device, a 3D geometric shape like a Hoberman Ball to move suture ends (placed into parts of the ball and being held by couplers 1511 when the ball is in its expanded configuration) into a knot configuration (created by collapsing the ball inwards) FIG. 15.

Figure 16B:
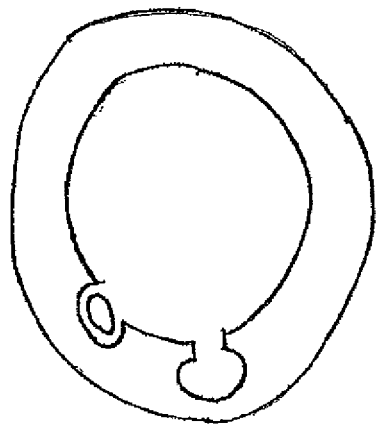
FIGS. 16A and 16B are drawings show a sixteenth embodiment of the knot tying accessory having cam paths that a ball bearing can follow.
Figure 16A:
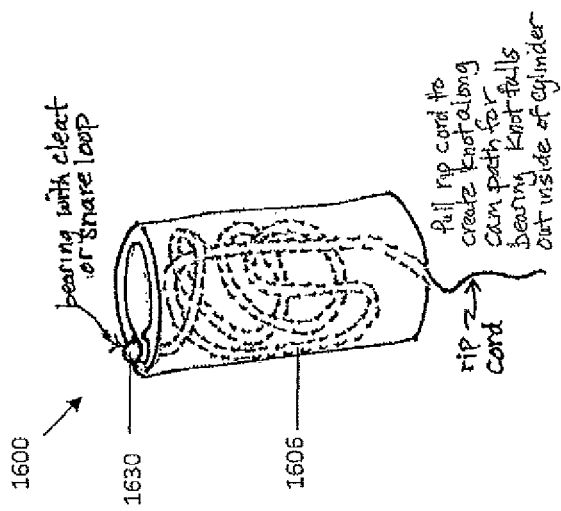

In yet another variation of the knot tying accessory device, a concept of cam paths 1606 that a ball bearing 1630 follows is shown in FIGS. 16A and 16B. The ball bearing has a cleat or snare loop 1611 to hold onto a suture end. A cord is attached to the bearing such that when it is pulled, the ball bearing attached to the suture follows the path to tie a knot. The suture can then drop to the interior of the cylinder and the knot is released. The cam path can move radially, circumferentially, and axially to form complex knot patterns with overlapping sections. A variation of the previous embodiment is shown in FIGS. 16A and 16B where cam paths with a cleat that spins along and up the cam path to wrap the suture around the post strand. At the end, the cam springs back down with one half spin to complete SMC knot. A possible cleat shape is shown in FIG. 16B.

Another variation of the knot tying accessory device is shown in FIGS. 17A and 17B. In this variation on the embodiment directly before, the cam paths includes a cleat 1736 that spins along and up the cam path to wrap the suture around the post strand. At the end, the cam springs back down with one half spin to complete SMC knot. A possible cleat shape is shown in FIG. 17B.

Figure 18:
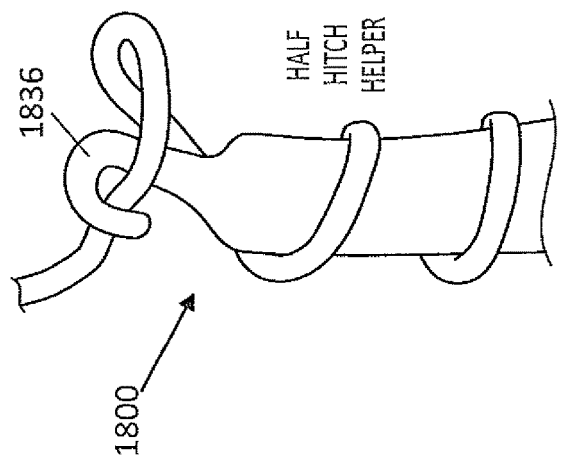
FIG. 18 is a drawing showing a tool for easily forming a half hitch.

Also disclosed are concepts for a tool for quickly forming half-hitches in a suture (FIG. 18). The tool has a long body and a hook 1836 at one end. The suture is wrapped around the shaft of the tool, and then the hook is used to pull the suture through the wrap, forming a half hitch. The shaft of the tool has a greater diameter than that of the hook.

Figure 19:
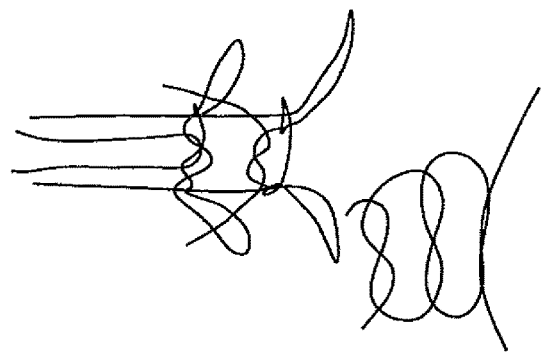
FIG. 19 is a drawing showing the formation of a stronger knot using two snares.

Also disclosed herein are concepts for tying a stronger knot (FIG. 19). The concept below shows a knot pusher that forms and tightens square knots at the repair site. The knot pusher (shown in green below) has pairs of snares at the distal end, and the suture ends would be snared in and pulled tightly in directions perpendicular to the axis of the knot pusher to create levels of a square knot (shown in orange). A first set of snares may be nested into a second set of snares, so that the first set of snares may be pulled to form the first level of the knot, then pull the suture into the second set of snares. The second set of snares can then be pulled to form the second level of the knot. Further nested sets of snares may be used to form an arbitrary number of levels of the knot to increase the knot strength. A variation of the previous concept creates half hitches at the end of the knot pusher, which then facilitates tightening those half hitches. This might be accomplished by a different configuration of snares. This may also be accomplished by a rotating member of the knot pusher that forms a suture line into a half hitch pattern.

Figure 20:
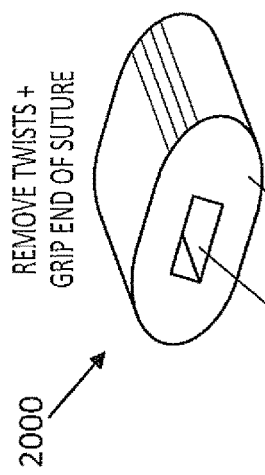
FIG. 20 is a drawing of a knot tying accessory device that are implantable.

The following knot tying accessory devices are implantable devices. FIG. 20 shows one example of such a device. Here, a short tube or sleeve implant 2001 that would be crimped closed around the suture ends having a holder 2011. One embodiment is a metal sleeve that is overmolded with plastic to soften the contact surfaces and prevent chondral tissue damage. The sleeve could also be sized to remove twists from the sutures to increase the holding strength.

Figure 21:
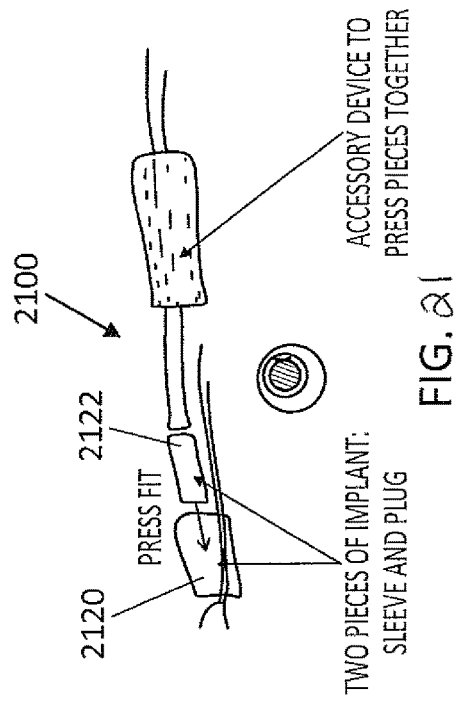
FIG. 21 is a drawing of a second embodiment of an implantable knot tying accessory device having a sleeve and a plug.

Another embodiment of an implantable knot tying accessory is shown in FIG. 21. Here, a suture that is slid through an implantable sleeve 2120, and then a plug 2122 is pressed into the sleeve to trap the suture in place. Pressing the two portions together may be accomplished by an accessory device. In some examples, an implantable clip that squeezes shut to hold the suture ends and close the repair loop. In other examples, an implantable clip that squeezes shut to hold the suture ends and close the repair loop. In yet other examples, an implantable rotating clasp holds the suture ends in place. Initially, the top and bottom pieces of the clasp are aligned so that there is a straight lumen through which the sutures can slide. Once the repair is appropriately tensioned, the one of the ends of the clasp is rotated so that the suture pathway becomes tortuous and small, thus holding the suture in place. In other examples, the implantable accessory is a clip that snaps shut to hold the suture ends to close the repair loop.

In yet other examples, the implantable accessory 2200 is an implantable clasp that is able to hold suture ends in place (FIGS. 22A-22C). In a first position, a top piece 2220 and a bottom piece 2222 of the clasp are aligned so that there is a straight channel through which a suture can slide. Once the repair is appropriately tensioned, one end of the clasp may be rotated so that the suture pathway become tortuous and small, thus holding the suture in place.

Figure 23:
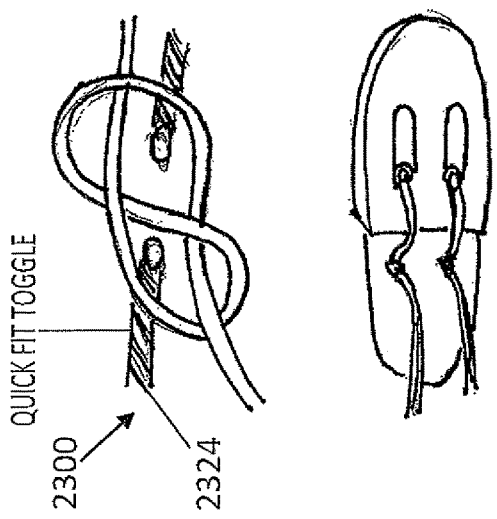
FIG. 23 is a drawing showing another embodiment of an implantable knot tying accessory device having an implantable toggle.

Another embodiment of an implantable knot tying accessory 2300 is shown in FIG. 23. An implantable toggle 2324 has a configuration where the suture slides easily through it, and a second where the suture is held in place. The mechanism could be similar to the toggles on drawstrings on clothing, where pushing a button aligns the holes through which the suture travels. The toggle could have separate lumens each suture, or potentially a single hole for both sutures.

Figure 24:
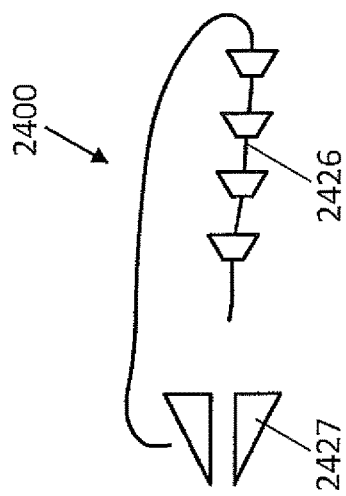
FIG. 24 is a drawing showing another embodiment of an implantable knot tying accessory device having a structure for bringing together and maintaining tissue.

FIG. 24 shows a structure for bringing together and maintaining tissue. This embodiment includes a one-way sliding mechanism 2426 like a zip tie to hold the meniscus together. One embodiment of this concept uses an implantable, non-suture based material to form a holder 2427 portion of the zip tie. Another embodiment uses barbed suture as the incremental teeth of the zip tie. Another embodiment uses a series of knots tied into a suture line as the incremental teeth of the zip tie. Yet another embodiment of the holder is the existing suture line, which the barbed suture or knots is pierced through to keep in place.

Figure 26:
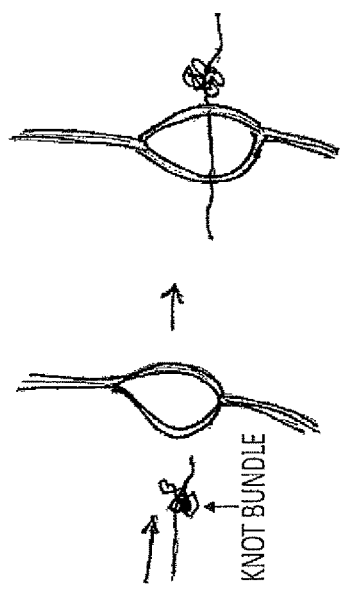
FIG. 26 is a drawing showing a variation of concept for bringing together and maintaining tissue is a suture with knots having a loop formed from dividing the width of the suture in two.
Figure 27B:
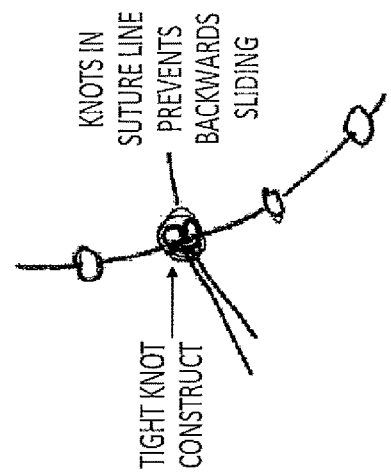
FIGS. 27A and 27B is a drawing showing a suture line with knots can also be slid through a pre-tied, sliding knot construct such as a girth hitch.
Figure 27A:
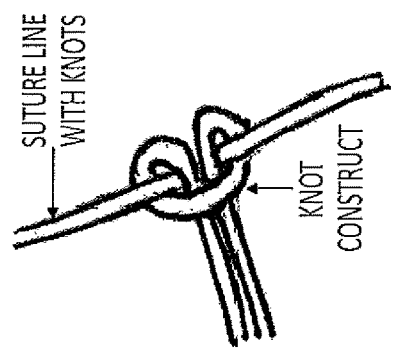
Figure 25:
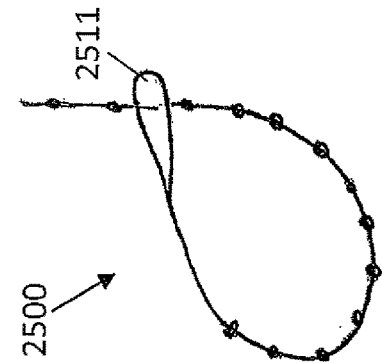
FIG. 25 is a drawing showing another concept for bringing together and maintaining tissue is a suture with knots.

Another concept for bringing together and maintaining tissue is a suture with knots 2500, wherein the suture can also be passed through a loop 2511 formed from the suture (FIG. 25). Once the repair is tight, the loop would automatically be pulled tight and shut, keeping the suture knot from pulling out. A variation of this idea uses a loop formed from dividing the width of the suture in two. Such a loop could be anywhere on the suture length (FIG. 26), not only at the end of the suture. The appropriate suture knot/ball is passed through the loop to hold the repair closed. The suture line with knots can also be slid through a pre-tied, sliding knot construct such as a girth hitch. When the repair was appropriately tensioned, the free leg of the knot construct is pulled to cinch down on the suture, and the suture knots keep that line from sliding backwards (FIGS. 27A and 27B).

Another embodiment of the knot accessory 2800 is shown in FIG. 28. shows an implant similar to a backpack strap, which uses a tortuous path and material shaping so that it is easy to pull the suture through in one direction but difficult in the reverse direction.

Another embodiment of the knot accessory 2900 is shown in FIG. 29. This device includes an outer tube 2920 and an inner tube 2922 that are initially in an open configuration allowing the sutures to easily slide through. To secure the suture in place, the tubes are slid and held together, creating a tortuous path for the suture and preventing them from sliding further.

Another embodiment of the knot accessory is shown in FIG. 30. Here a suture bight through a hole 3020 in an implant 3022. The ends of the suture are passed through the suture bight, and the loop construct is tightened.

Another embodiment of the knot accessory 3100 is shown in FIG. 31. Here, adhesive are used to bond the suture lines together, or to bond a suture knot. One version uses an adhesive activated by aqueous solution. One version delivers the adhesive from an accessory device at the repair site, and another version delivers the adhesive through a knot pusher. The suture can also be welded together. Methods exist currently to weld the suture ultrasonically. The welding could be facilitated at the end of a knot pusher/knot cutter device. In FIG. 31, a mesh/grid material 3130 through which the suture is woven. The suture can slide easily through the mesh to tighten the repair, until the mesh is tightened, folded, and/or rolled up. In one variation, the mesh starts attached to one end of the suture (see bottom picture below). In another variation, the mesh is a separate piece through which both suture ends are woven after stitch delivery through the meniscus.

A last concept described herein is the idea of a doubled-back suture. A doubled-back suture in the repair to create a stronger knot. The doubled-back suture could be achieved by shuttling in the bight of suture. Alternately, the doubled-back suture could be created by passing a bight of suture on one needle fire, and passing both free ends of suture on the other fire. Another variation uses a knot configuration that is not traditionally considered a sliding knot using lubricious suture that enables the knot to be slid. This can result in a more secure knot in the lubricious suture than would be possible using a traditional sliding knot. This style of knot may be formed by a cartridge or accessory device as detailed above. The knot may also be formed at the end of a knot pusher for convenient repair completion. Another variation forms a non-sliding knot around the tip of a knot delivery device (for example, a knot pusher) such that it is held in an open and sliding configuration. The knot is then delivered to the repair and released from the knot delivery device, allowing the knot to be tightened into a non-sliding configuration to complete the repair loop. One embodiment of such a knot is shown in the document entitled "150903 Knot Tying Accessory Invention Disclosure." One embodiment is a cartridge that attached to the knot delivery device. Another embodiment is a separate accessory device that does not attach to the knot delivery device. Another embodiment is a knot delivery device with built-in knot-forming functionality.

In any of the embodiments described above, a second suture may be placed about the repair suture to further maintain and hold the repair suture in place. Also, in any of the embodiments described above, the knot tying accessory can be provided for as a kit. It may also be advantageous for the kit to be sterile.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the ten is "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of tying a suture knot in a repair loop comprising:
    attaching a suture snare to a suture management device, the suture snare having a snaring end, a second opposing end and a loose knot therebetween and wherein attaching disposes the loose knot around a shaft of the suture management device;
    coupling a repair suture to tissue;
    threading a first end of the repair suture through the snaring end;
    drawing the snaring end and repair suture first end through the loose knot so as to replace the loose knot with the repair suture first end and thereby form a repair suture loose knot around the suture management device;
    transferring the repair suture loose knot over a second end of the repair suture operatively coupled to the suture management device to form a repair knot.

2. The method of claim 1 wherein the suture management device is a knot pusher.

3. The method of claim 2 further comprising loading the repair suture second end into the knot pusher.

4. The method of claim 1 wherein the suture management device is a suture passer comprising a pair of jaws.

5. The method of claim 4 further comprising coupling the repair suture to tissue with the suture passer, and then removing the repair suture first end from the suture passer before threading the repair suture first end through the snaring end.

6. The method of claim 4 wherein attaching the suture snare further comprises simultaneously operatively coupling the repair suture to the suture management device.

7. A method of tying a repair knot around tissue comprising:
    attaching a cartridge including a suture snare to a suture management device, the suture snare having a snaring end, a second opposing end and a loose knot therebetween, the loose knot operatively coupled to a shaft of the suture management device;
    coupling a repair suture to tissue;
    threading a first end of the repair suture through the snaring end;
    drawing the suture snare through the loose knot so as to form the repair suture first end into a loose knot; and
    transferring the repair suture loose knot over a second end of the repair suture operatively coupled to the suture management device to form a repair knot.

8. The method of claim 7 wherein the suture management device is a knot pusher.

9. The method of claim 8 further comprising loading the repair suture second end into the knot pusher before transferring the repair suture loose knot over the second end.

10. The method of claim 7 wherein the suture management device is a suture passer comprising a pair of jaws.

11. The method of claim 10 further comprising coupling the repair suture to tissue with the suture passer, and then removing the repair suture first end from the suture passer before threading the repair suture first end through the snaring end.

12. The method of claim 7 wherein attaching the suture snare further comprises simultaneously coupling the repair suture to the suture management device.

13. A knot tying accessory cartridge for cooperating with a suture management device comprising:
a snare having a first end, a snaring end and a loose knot therebetween, wherein the loose knot is a locking and sliding knot and is configured to wrap around a shaft of the suture management device; wherein the snaring end is configured to receive a first end of a repair suture, and wherein tension on the suture snare first end is operable to draw the repair suture first end so as to replace the suture snare loose knot and form a repair suture loose knot wrapped around the suture management device shaft.

14. The knot tying accessory of claim 13 wherein the suture management device is a knot pusher.

15. The knot tying accessory of claim 14 wherein the knot pusher is configured to engage with a repair suture second end, such that the repair suture loose knot may be transferred over the second end and form a repair knot.

16. The knot tying accessory of claim 13 wherein the suture management device is a suture passer, comprising a pair of jaws.

17. The knot tying accessory of claim 16 wherein the repair suture loose knot may be transferred over the pair of jaws and over a repair suture second end loaded within the suture passer to form a repair knot.

18. The knot tying accessory of claim 16 wherein the suture management device is a suture passer pre-loaded with the repair suture such that the first end of the repair suture is operatively removed from a jaw of the pair of jaws before loading into the suture snare.

19. The knot tying accessory of claim 13 wherein the repair suture is preloaded within the knot tying accessory cartridge.

* * * * *